United States Patent [19]

Schmitt-Thomas

[11] Patent Number: 5,001,923
[45] Date of Patent: Mar. 26, 1991

[54] PROCESS TO MEASURE THE WETTING FORCES BETWEEN A LIQUID AND A SOLID BODY

[76] Inventor: Karlheinz G. Schmitt-Thomas, Sophie-Stehle-Strasse 12A, 8000 Munchen 19, Fed. Rep. of Germany

[21] Appl. No.: 462,484

[22] Filed: Jan. 10, 1990

[30] Foreign Application Priority Data

Jan. 13, 1989 [DE] Fed. Rep. of Germany ....... 3900845

[51] Int. Cl.⁵ .......................................... G01N 13/02
[52] U.S. Cl. .................................................. 73/64.4
[58] Field of Search ........................................ 73/64.4

[56] References Cited

U.S. PATENT DOCUMENTS 4,754,640  7/1988  Fitzgerald et al. ....................... 73/54

FOREIGN PATENT DOCUMENTS

| | | |
|---|---|---|
| 0297032 | 12/1988 | European Pat. Off. . |
| 1010397 | 6/1957 | Fed. Rep. of Germany . |
| 2258429 | 8/1973 | Fed. Rep. of Germany . |
| 3306406 | 7/1984 | Fed. Rep. of Germany . |
| 3741558 | 7/1988 | Fed. Rep. of Germany . |
| 3714012 | 11/1988 | Fed. Rep. of Germany . |
| 2588664 | 4/1987 | France . |
| 23436 | 2/1980 | Japan ..................................... 73/64.4 |
| 82039 | 6/1980 | Japan ..................................... 73/64.4 |
| 97427 | 6/1982 | Japan ..................................... 73/64.4 |
| 152339 | 6/1989 | Japan ..................................... 73/64.4 |
| 658442 | 4/1979 | U.S.S.R. ............................... 73/64.4 |
| 1241104 | 6/1986 | U.S.S.R. ............................... 73/64.4 |

OTHER PUBLICATIONS

Journal of Physics E. Scientific Instruments, vol. 17, 1984, pp. 569–572.
Schmitt-Thomas, Becker, Groll; "Lötbarkeitsprüfung an SMDs mit der Benetzungswaage", Elecktronik Produktion & Prüftechnik, Oct. 1987, pp. 48–54.
Jillek, Wolf; "Eine Rechnergestützte Lötbarkeitsprüfung nach dem Prinzip der Benetzungswaage", Elektronik Produktion & Prüftechnik, Apr. 1983, pp. 149–152.

Primary Examiner—Hezron E. Williams
Assistant Examiner—Joseph W. Roskos
Attorney, Agent, or Firm—Fidelman & Wolffe

[57] ABSTRACT

A process to measure the moisture permeability between a liquid and a solid body is described, which is of importance for determining the suitability of material combinations. In the course of the process, the oscillation behavior of an oscillating system is changed when a solid body or test object is immersed in a liquid by the interaction of surface tension forces between the surface of the solid body or test object and the fluid. The change in the oscillation behavior or the transfer of oscillation energy between the solid object and the fluid is then used as an indicator of the strength of the surface tension force.

20 Claims, 5 Drawing Sheets

$C_0$ CAPACITY OF THE TRANSDUCER FAR BELOW THE RESONANCE FREQUENCY MINUS $C_1$, $R_1$ RESISTANCE DUE TO MECHANICAL LOSS, $R_L$ RESISTANCE OF THE LOAD, CAUSED BY ENERGY RADIATED; IN VACUUM $R_L = 0$, $C_1$ CAPACITY OF THE MECHANICAL CIRCUIT $L_1$ INDUCTIVITY OF THE MECHANICAL CIRCUIT

PROCESS TO MEASURE THE WETTING FORCES BETWEEN A LIQUID AND A SOLID BODY

The invention concerns a process to measure the wetting forces between a liquid and a solid body.

The hydrophilic force between a liquid and a solid medium plays a significant role in the determination of the suitability of combinations of materials, in particular for the formation of a joint or adhesive layer between various materials. Areas of application include, for example, the insertion of reinforcing fibers during the manufacture of composite materials. In surface bonds, the moisture absorbing characteristics between the individual fibers is also often very important for the quality of the bond. Measurement of the surface tension and thus the wetting forces plays an extremely vital role in the determination of solderability, in particular in the areas of electronics and microelectronics.

The reliability of parts and components in the fields of electronic technology and electronics is to a great degree dependent on the faultless production of the soldered connection, in particular between the individual components and the printed circuit board. Soft soldering is the single most important process during large scale manufacture of electrically conductive connections. With today's production methods, those soldering processes which permit a high degree of automation have taken on particular significance. These processes include wave soldering, drag soldering, reflow soldering and combinations of these processes or soldering methods which are derived from them.

In order to ensure an unvarying product quality which can be monitored, and thus the required level of reliability, it is essential that the solderability can be quantitatively and reproducibly measurable. Solderability is directly tied to the hydrophilic characteristics between the solder and the substrate. The wettability process consists of a reaction which takes place at the three-phase border of three materials: the solder, the solid substrate and the surrounding medium. Thus, the wettability is dependent on the type and the surface condition of the substrate material, the temperature, the composition and condition of the solder, as well as the flux. Various processes are employed to determine the wettability. The following represent the most important methods:

1. Optical test;
2. Diffusion measurement in accordance with DIN 8516
3. Stroke immersion test in accordance with DIN 32506, Parts 2, 3;
4. Hydrophilic attraction test in accordance with DIN 32506, Part 4;
5. Solder sphere test in accordance with DIN IEC 68, Part 2 to 20;
6. Rotation immersion test in accordance with DIN 40803, Part 1;
7. Bouyancy height test The measurement of the forces dependent on time when the test object is submerged in the solder bath plays a significant role in determining the solderability, since this method can be employed to obtain a series of reproducible and meaningful numerical values. The procession of the forces over a period of time, which are to be measured by means of an hydrophilic scale during the immersion step result from the fact that, when a test object to be soldered is submerged in the solder, the surface tension and the frictional forces arising from the viscosity of the solder and from the penetration of the oxide surface (FIG. 1a) must first be overcome. As the wetting process begins to take effect, the surface tension forces become active allowing either the solder to rise along the surface or pulling the test object into the solder. Finally, the buoyancy of the test object also acts to counter the surface tension forces (FIG. 1b). Illustrative plots are shown in FIGS. 2a–c. The wettability curve is the result of the progression of the forces during the period of time over which the test object is submerged in the solder bath, and provides a reproducible means of quantitatively depicting solderability. The force/time graph developed with the aid of the hydrophilic scale reflects the progression of the processes which take place upon immersion (FIG. 3). Measurements of surface tension forces by means of the hydrophilic scale have been subject to variations, in particular with respect to more precisely determining the start of the wetting process and/or the separation of the solder when the test object is removed from the solder bath. Deviations from standard, vertical immersion by the application of various angles of immersion have also been employed.

The variations in the processes for measuring the wetting forces with the aid of the hydrophilic scale arise in part from the difficulty in determining the solderability of miniaturized components, in particular for components used in SMD technology. Because of the small amount of expansion of the surfaces to be metal-coated, a complete solder meniscus cannot form on SMD components. Thus, the ascent of the meniscus when components such as SMDs are submerged is limited by the metallic coating already present, and is therefore no longer characteristic for the wettability. This is reflected in moisture permeability curves by the fact that the maximum wettability of geometrically equal parts always ends at the same level, regardless of the test parameters. Thus, under these preconditions, the only differentiation which can be made is between wettability or no wettability while the quantitative measurement of the wettability cannot be made in the manner of standard, wettability curves developed for components without a geometrically dependent limitation to the meniscus (FIG. 3).

It is the object of the invention to develop a process to measure the surface tension forces between a liquid and a solid, which will permit a quantitative measurement of the surface tension forces.

BRIEF DESCRIPTION OF THE DRAWINGS

FIG. 3b is a graph of a wetting curve corresponding to FIG. 3a;

Figure 1A:
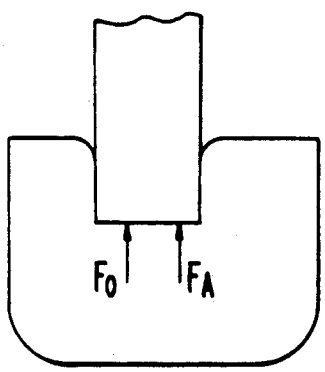
FIG. 1a is a cross-sectional view of a test object initially inserted in solder.
Figure 1B:
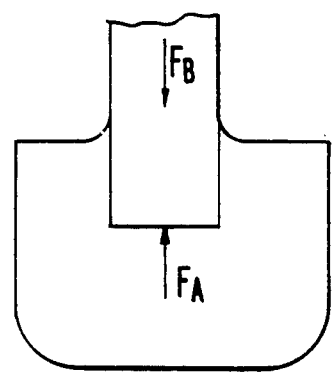
FIG. 1b is a cross-sectional view of the test object inserted in solder after a period of time.
Figure 2A:
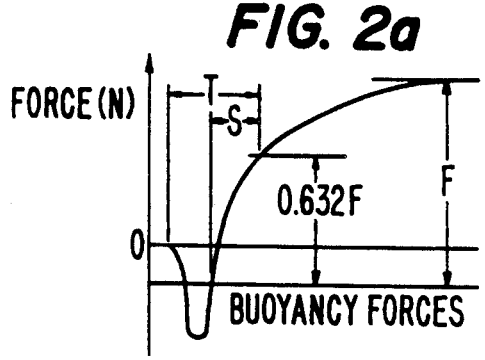
FIG. 2a is a graph showing a moisture permeability curve.
Figure 2B:
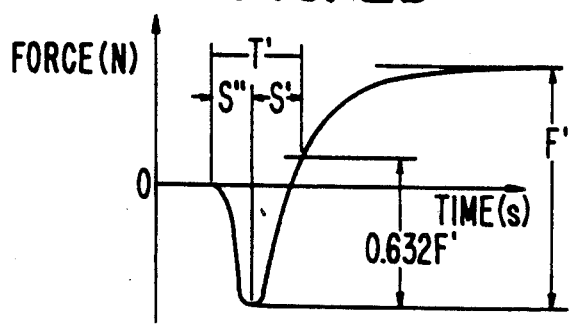
FIG. 2b is a graph showing another moisture permeability curve.
Figure 2C:
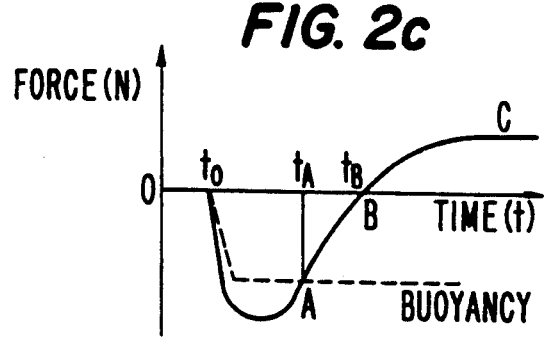
FIG. 2c is a graph showing yet another moisture permeability curve.
Figure 3A:
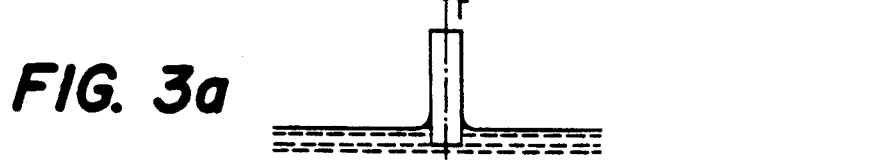
FIG. 3a is a cross-sectional view of a wire component of known geometry inserted in solder.
Figure 3B:
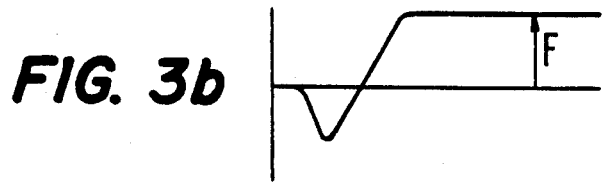
Figure 3C:
FIG. 3c is a cross-sectional view of an SMD component inserted in solder wherein the geometry of the component is not exactly known.
Figure 3D:
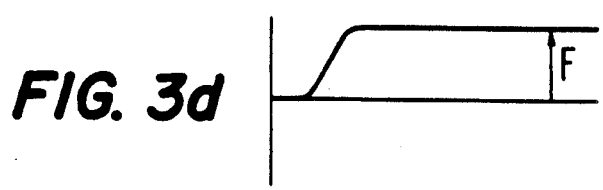
FIG. 3d is a graph showing a wetting curve corresponding to FIG. 3c.

The process in accordance with the invention is based on the supposition that the wettability is a result of the driving forces of surface diffusion, that is, that it follows the attempts of a surface to saturate itself with atoms from the surrounding medium to a point where minimum energy results. In contrast to the hydrophilic scale, which measures static forces over a period of time for this process, the process in accordance with the invention determines the forces active during a dynamic process such as is represented by an oscillation. The effects of the forces active during the wetting process cause the oscillating system - of which the test object is a part - to experience a change, for example by a dampening of the frequency shift resulting from an energy transfer between the solid and the liquid, which results in the entire solid/liquid system is affected by the oscillation of one component. The measurement of the damping effect or frequency shift is not limited by the expansion of the metal-coated surfaces, and can thus be performed even when very limited metal-coated surfaces are present. In addition, an oscillating system reacts much more sensitively to changes than is the case with static measurements.

In order to perform the measurements in accordance with the invention, a system with a test object is preferred which can be subjected to longitudinal or torsional oscillation; transverse oscillation and surface oscillation can also be reasonably employed. A single frequency such as, for example, the resonance frequency of the system (pick-up and probe) can be selected. On the other hand, all frequencies within a specific range can be employed in order to produce a variation in the system. In the case of a variation, the influence of the surface tension forces as dependent on the frequency setting can be observed. In addition to measuring the dampening and/or shift of the frequency or frequencies, the oscillation energy transferred across the liquid/solid interface, which also supplies information concerning the surface tension forces, can also be employed. Measurement of the energy arising from the transfer across the liquid/solid interface can also be used by itself. In order to measure the transferred energy, a sonic sensor which receives the transmitted energy at another point (in the bath or on the solid body) is required in addition to the system to be energized.

In order to measure the surface tension forces and their influence on the oscillating test object, the amplitude can be selected in such a manner that at the minimum of the wave (its lowest point), the body is barely in contact with the bath so that, as the wave proceeds to its maximum, the bath is drawn upward by the surface tension forces. By varying the height of the amplitude, the maximum point at which the meniscus is torn off can be determined. Measurement of the dampening of the oscillation as a result of the forces between the bath and the solid body surface (surface tension forces) can, however, also be made with a fully submerged test object. Both the amplitude as well as the frequency can either remain constant or can be varied during the test procedure.

Figure 4:
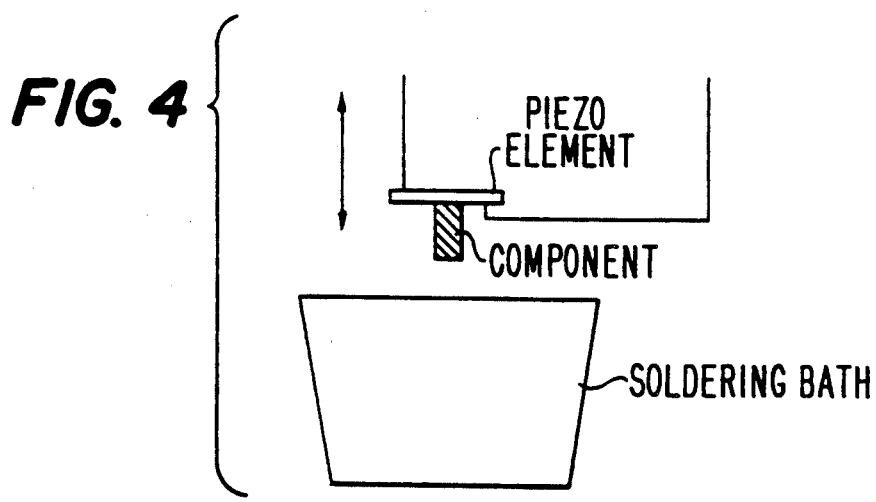
FIG. 4 is a schematic drawing recording to one embodiment of the invention.

An example of the embodiment of the invention shows the influence of the surface tension forces on the frequency. The component to be tested is securely connected to a piezoelectric plate, for example by adhesion. The application of an alternating current causes the piezoelectric/component system to oscillate in, for example, sinusoidal waves, thus displacing the component parallel to its longitudinal axis (FIG. 4). In this case, the frequency is selected in such a way that no self-oscillation of the test object occurs. If the oscillating system is now immersed in the solder bath, two effects occur as a result of surface tension:

1. The systems characteristic frequency is shifted by the surface tension forces.
2. The oscillation is dampened in direct proportion to the degree of moisturization taking place.

Figure 5:
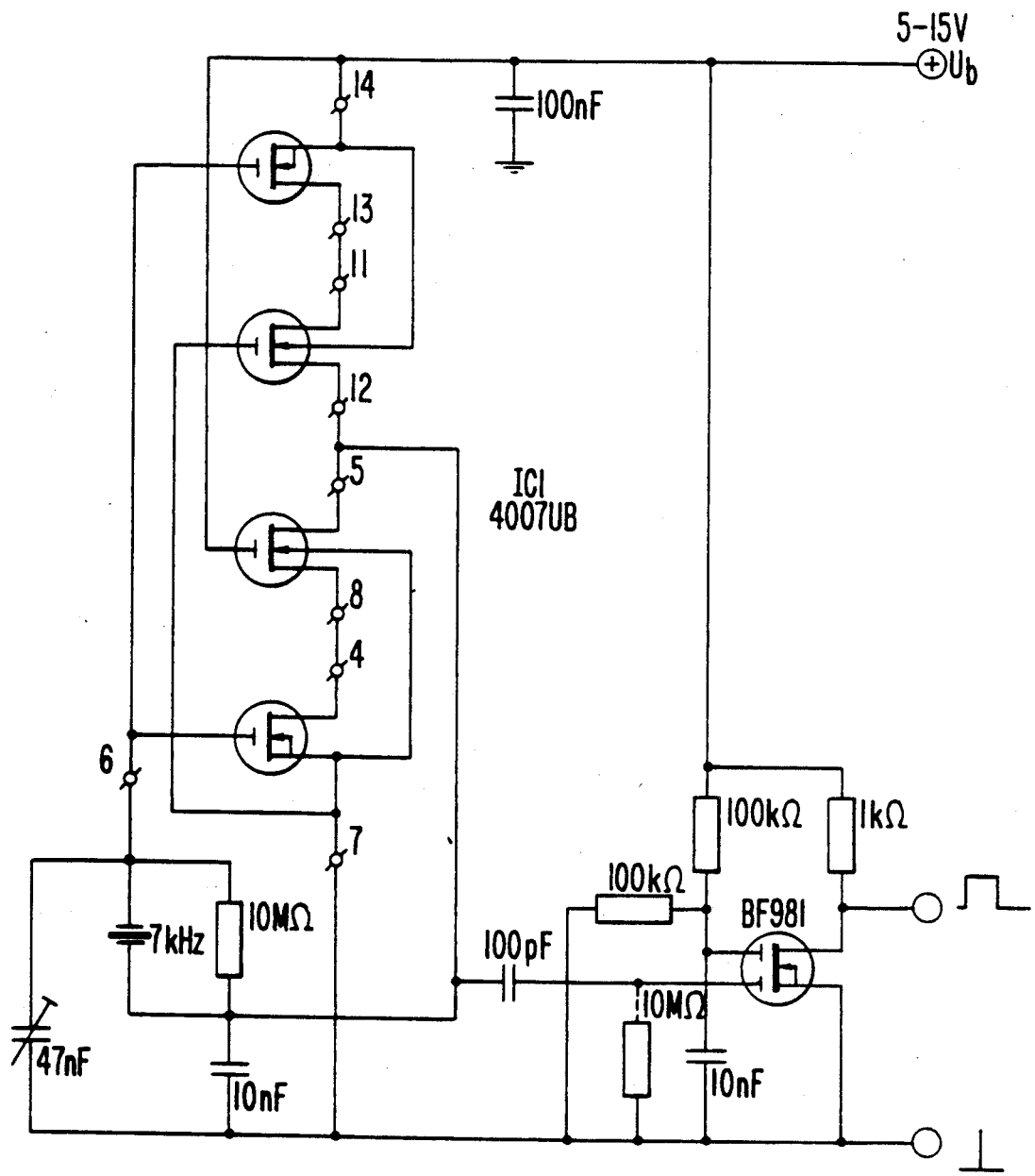
FIG. 5 is a schematic diagram of an embodiment of the oscillator circuit according to the invention.
Figure 6:
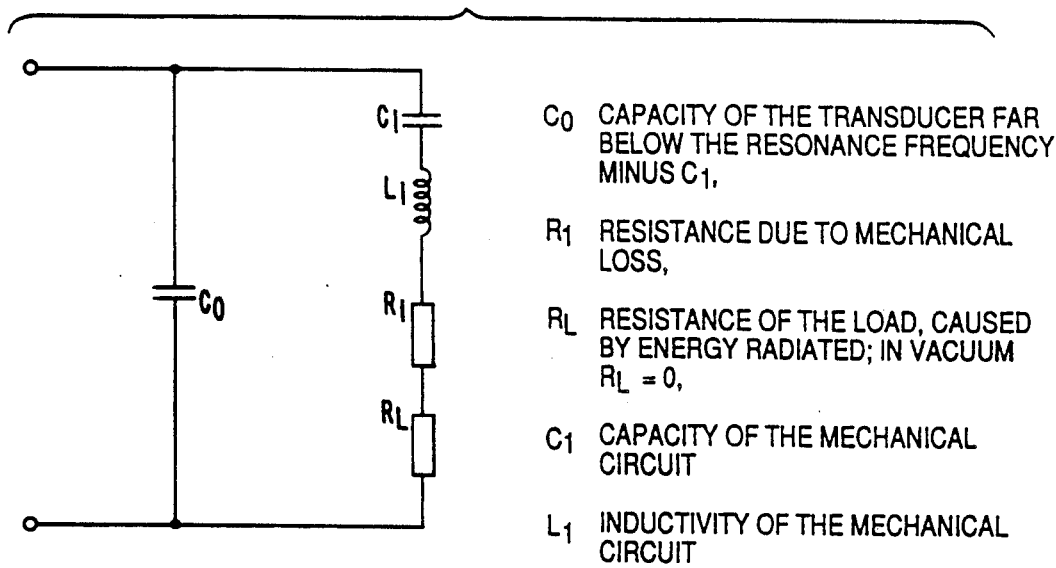
FIG. 6 is a schematic diagram of an equivalent circuit according to the invention.

In order to measure the change in the resonance frequency, the oscillating quartz can, for example, be employed as the frequency-determining link in an oscillator circuit (FIG. 5). The change in frequency over time will then reflect the course of the wetting. The dampening which arises as the result of surface tension forces causes an increase in the resistance $R_L$ in the equivalent circuit of the oscillating quartz and can therefore be measured via the admittance as resonance (FIG. 6).

Figure 7:
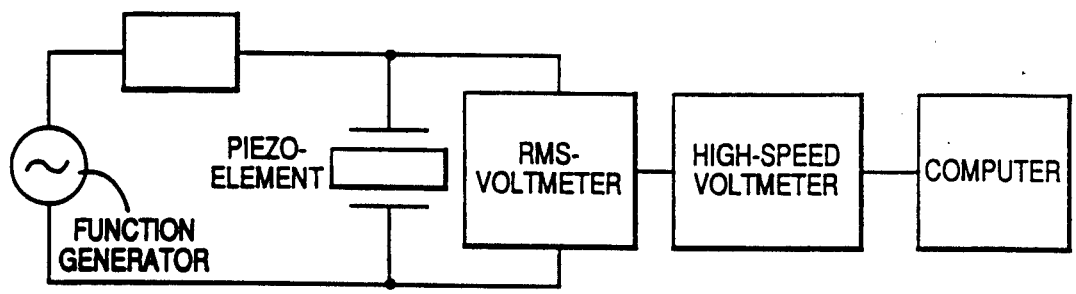
FIG. 7 is a schematic block diagram of a metering system according to the invention.

MELF (Metal Electrode Face Bonding) type SMD resistors measuring 5.9×2.2 mm as well as a Valvo piezo-oxide oscillator membrane (12.5 mm diameter, 12 kHz resonance frequency, 6 nF capacitance) were employed. The admittance of the piezoelectric part was measured. In order to measure the wettability the function generator was set at the frequency at which the admittance displayed its maximum value. The metering system is shown in FIG. 7. If the test object id immersed in a solder bath and the frequency of the function generator remains constant, the admittance changes due to the following factors:

1. The characteristic frequency of the piezoelectric part is shifted because of the arising, time-dependent forces, so that the maximum admittance occurs at a point other than the set frequency.
2. The system is dampened by the permeation of the solder, which produces a reduction of the admittance.

Figure 8:
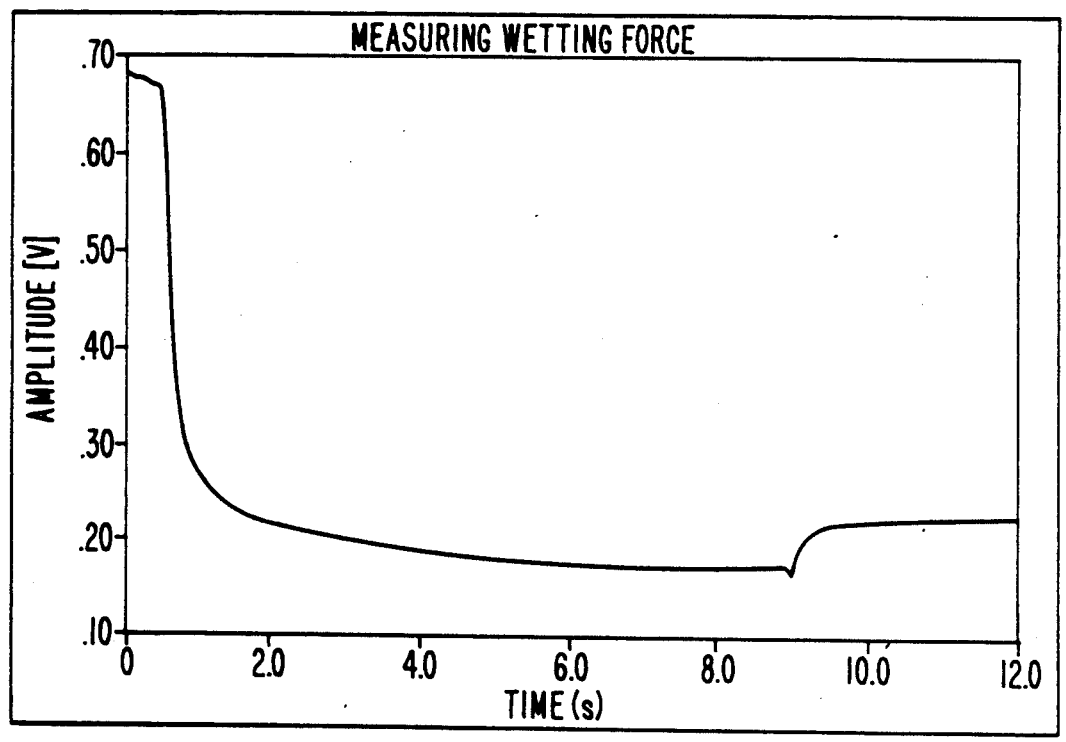
FIG. 8 is a graph showing the admittance progression with no moisturizing.
Figure 9:
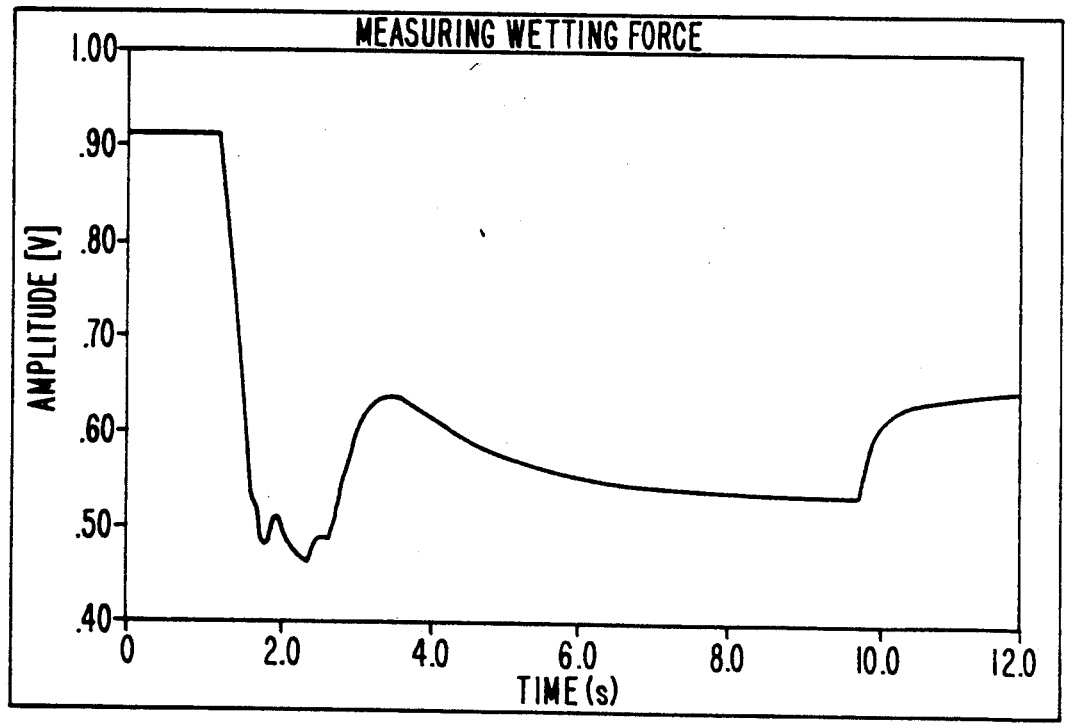
FIG. 9 is a graph showing the admittance progression with moisturizing.

Temperature changes which can influence the frequency must either be prevented or compensated for. The curves plotted from the data obtained from the test set up (FIG. 8 and FIG. 9) depict the admittance progression for both wetting and no wetting. FIG. 9 clearly shows that additional forces caused by the wetting process appear in the curve as well as how the dampening effect of wetting manifests itself.

Interpretation of the progression of the admittance (FIG. 9) permits differential deductions concerning the surface tension forces and thus the solderability of components to be made. These deductions go far beyond those of previously employed wettability tests.

Many modifications of the above described embodiments are possible without departing from the spirit and scope of the invention. For example, a solid body may be brought into contact with a moisturizing medium while the medium is still in its solid state, whereby, as the moisturizing medium is liquified, the change in the dampening and/or frequency of the oscillating body brought about by the rising surface tension forces may then be measured. In addition, a measurement may be carried out with a flowing medium rather than with a medium which is at rest. Furthermore, the test object, rather than being directly connected to the oscillator, can be connected by negative pressure or magnetic force to a suitable holder or clamp which is, in turn, connected to the oscillator. This holder may be used to hold several test objects in such a way that they may be either simultaneously immersed in the moisturizing liquid or be immersed individually. The test object may also be immersed at a desired angle rather than vertically. Therefore, the scope of the invention is measured not by the disclosed embodiments, but by the appended claims.

What is claimed is:

1. A process to measure the wetting forces between a liquid solder metal and a solid soldering substrate, comprising the steps of:
   connecting the solid soldering substrate to a oscillating system;
   immersing the solid soldering substrate into the liquid soldering metal;
   measuring oscillation behavior of the solid soldering substrate, immersion depth and elapsed time; and
   determining the wetting forces from results of the measuring step.

2. A process as claimed in claim 1, wherein the measuring step comprises subjecting the solid soldering substrate to various oscillating modes after immersion into the liquid soldering metal and recording changes in oscillation over time; and wherein characteristic values for the wetting forces of the solid soldering substrate are determined from time-dependent dampening and frequency changes of oscillation during immersion.

3. A process a claimed in claim 1, wherein the solid soldering substrate is not completely immersed in the liquid, but rather comes into contact with the surface of the liquid soldering metal as a result of the oscillation.

4. A process as claimed in claim 1, wherein the solid soldering substrate is brought into contact with the liquid soldering metal while the metal is in a solid state, and wherein the measurements are made while the metal is liquified.

5. A process as claimed in claim 1, wherein the measuring step further comprises measurement of oscillation energy.

6. A process as claimed in claim 5, wherein only oscillation energy brought about by the wetting and the bonding of the liquid soldering metal is measured.

7. A process as claimed in claim 1, wherein the measuring step is carried out with a flowing liquid solid metal.

8. A process as claimed in claim 7, wherein the temperature of the flowing liquid soldering metal is varied during measurement.

9. A process as claimed in claim 1, wherein the solid soldering substrate is connected by negative pressure or magnetic force to a holder, wherein said holder is firmly connected to the oscillator.

10. A process as claimed in claim 9, wherein several test objects are mounted in the holder so that they may either be simultaneously immersed or immersed individually.

11. A process as claimed in claim 1, wherein the solid soldering substrate is immersed at a desired angle in the liquid soldering metal.

12. A process as claimed in claim 1, wherein oscillation is induced in the liquid soldering metal, and wherein energy therefrom transferred to the solid soldering substrate is measured.

13. A process as claimed in claim 1, wherein oscillation is induced in the solid soldering substrate, and wherein the energy therefrom transferred to the liquid soldering metal is measured.

14. A process as claimed in claim 1, wherein a specific frequency is selected for oscillation.

15. A process as claimed in claim 14, wherein the specific frequency is the resonance frequency of the system.

16. A process as claimed in claim 1, wherein variable frequencies within a desired frequency range are selected for oscillation.

17. A process as claimed in claim 1, wherein a constant amplitude is selected for oscillation.

18. A process as claimed in claim 1, wherein a variable amplitude is selected for oscillation.

19. A process as claimed in claim 1, wherein a sinusoidal oscillation is employed.

20. A process as claimed in claim 1, wherein a non-sinusoidal oscillation is employed.

* * * * *